(12) United States Patent
Rulo

(10) Patent No.: US 11,246,749 B2
(45) Date of Patent: Feb. 15, 2022

(54) WATERPROOF PERSONAL THERMOREGULATION SYSTEM FOR THE ACTIVE INDIVIDUAL

(71) Applicant: Neptune Performance Products LLC, Chesterfield, MO (US)

(72) Inventor: Jason Andrew Rulo, Chesterfield, MO (US)

(73) Assignee: Neptune Performance Products, LLC, Chesterfield, MO (US)

( * ) Notice: Subject to any disclaimer, the term of this patent is extended or adjusted under 35 U.S.C. 154(b) by 338 days.

(21) Appl. No.: 15/448,671

(22) Filed: Mar. 3, 2017

(65) Prior Publication Data
US 2017/0252207 A1    Sep. 7, 2017

Related U.S. Application Data

(60) Provisional application No. 62/303,363, filed on Mar. 3, 2016.

(51) Int. Cl.
*A61F 7/02* (2006.01)
*A61F 7/10* (2006.01)
(Continued)

(52) U.S. Cl.
CPC ............ *A61F 7/02* (2013.01); *A61F 7/03* (2013.01); *A61F 7/034* (2013.01); *A61F 7/106* (2013.01); *A61F 2007/0022* (2013.01); *A61F 2007/0027* (2013.01); *A61F 2007/022* (2013.01); *A61F 2007/0219* (2013.01); *A61F 2007/0234* (2013.01); *A61F 2007/0238* (2013.01); *A61F 2007/0257* (2013.01); *A61F 2007/108* (2013.01)

(58) Field of Classification Search
CPC .... A61F 7/03; A61F 7/106; A61F 2007/0258; A61F 2007/0279; A61F 2007/0257; A61F 7/02; A61F 7/034; A61F 2007/0022; A61F 2007/0027; A61F 2007/0219; A61F 2007/022; A61F 2007/0234; A61F 2007/0238; A61F 2007/108; A41D 13/002; A41D 13/0058
See application file for complete search history.

(56) References Cited

U.S. PATENT DOCUMENTS 4,676,247 A * 6/1987 Van Cleve ............... A61F 7/02
                                                     607/112
5,086,629 A * 2/1992 Dibrell ................. A41D 13/005
                                                        401/6
(Continued)

*Primary Examiner* — Eun Hwa Kim
*Assistant Examiner* — Adam Z Minchella
(74) *Attorney, Agent, or Firm* — Stinson LLP

(57) ABSTRACT

Disclosed are thermoregulatory systems. In particular, thermoregulatory devices are incorporated into garments for warming and cooling a user's body. Thermoregulatory devices are waterproof and breathable, which allow thermogenerators such as hot packs and cold packs, to remain dry while still allowing air flow such that thermogenerators using air-activated chemical reactants remain active. Thermoregulatory devices are particularly useful with garments maintaining the thermogenerators close to the body's core where they will be most effective. The thermoregulation systems advantageously allow a user to selectively position thermoregulatory devices in different regions of the user's body to self-regulate core body temperature.

18 Claims, 8 Drawing Sheets

(51) Int. Cl.
*A61F 7/03* (2006.01)
*A61F 7/00* (2006.01)

(56) References Cited

U.S. PATENT DOCUMENTS

| | | | |
|---|---|---|---|
| 2007/0106356 A1* | 5/2007 | Carstens | A41D 13/005 607/112 |
| 2007/0156213 A1* | 7/2007 | Friedensohn | A61F 7/03 607/114 |
| 2008/0040831 A1* | 2/2008 | Nilforushan | A41D 13/0058 2/69 |
| 2008/0141437 A1* | 6/2008 | Braunecker | A61F 7/03 2/206 |
| 2009/0299442 A1* | 12/2009 | Vergona | A47G 9/0215 607/114 |
| 2012/0004712 A2* | 1/2012 | Whitely | A61F 7/02 607/112 |
| 2014/0014101 A1* | 1/2014 | Stenzler | A61F 7/02 128/202.13 |
| 2014/0180369 A1* | 6/2014 | Oh | A61F 7/02 607/112 |
| 2015/0361599 A1* | 12/2015 | Minor | D03D 15/0088 442/92 |

* cited by examiner

WATERPROOF PERSONAL THERMOREGULATION SYSTEM FOR THE ACTIVE INDIVIDUAL

CROSS REFERENCE TO RELATED APPLICATIONS

This application claims priority to U.S. Provisional Application No. 62/303,363 filed on Mar. 3, 2016, which is hereby incorporated by reference in its entirety.

BACKGROUND OF THE DISCLOSURE

The present disclosure relates generally to a thermoregulation system. In an aspect, the thermoregulatory system is a waterproof body warming system. The waterproof body warming system uses a waterproof and breathable pouch designed for use with heat packs. The pouch can be used with a garment with a plurality of pockets each pocket designed to hold a pouch having a heat pack close to a user's body core for effective heat transfer to the user's body and maintenance of the user's core body temperature. In an aspect, the thermoregulatory system is a waterproof body cooling system. The waterproof body cooling system uses a waterproof and breathable pouch designed for use with cold packs. The pouch can be used with a garment with a plurality of pockets each pocket designed to hold a pouch having a cold pack close to a user's body core for effective heat transfer from the user's body and maintenance of the user's core body temperature.

Currently, a number of solutions are on the market for waterproof containers or pouches. Some of these solutions attempt to protect items by using plastic or rubber containers, but these solutions fail to meet the needs of the industry because these products do not "breathe"; that is, they do not allow air to pass through the container. Other solutions such as "dry bags" attempt to fill the need of a breathable waterproof container, but these solutions are similarly unable to meet the needs of the industry because they are large, backpack sized containers. No compact sized breathable waterproof container is believed to be on the market that allows a user to carry hot packs and cold packs in any easily affordable way. In addition, none of the products currently available are made to work specifically with an article of clothing to provide warmth to a user in wet environments after being submersed in water. Similarly, waterproof, breathable pouches for holding cold packs while allowing air current can be useful for transferring cool air to a user's body without allowing moisture to contact the user's body and/or clothing to provide a cooling effect in warm and hot environments.

It would be desirable to have thermoregulation systems that allow for thermoregulation of a user while protecting the thermogenerator from inactivation of the warming and cooling mechanisms. It would also be desirable to have thermoregulation systems that allow a user to selectively position thermogenerators in specific body regions, and thus, allow the user to regulate his or her core body temperature as desired while transitioning between cold and warm environments. In particular, it would be desirable to have a waterproof and breathable pouch that protects chemical heating packs while still allowing them to breathe, even after being exposed to water, which can inactivate chemical reactants used in commercially available hot packs. It would also be desirable to have a waterproof and breathable pouch to transfer cool air to the user's body (or heat away from the user's body) in warm environments or settings while preventing moisture from inactivating chemical reactants. Furthermore, it would be desirable to have these pouches be in a compact size to make it easier to carry in a garment having pockets specifically placed in regions of the garment that will maximize thermoregulation for the user. Accordingly, there currently exists a need in the industry for systems that allow chemical-based hot packs and chemical-based cold packs that use air circulation to continue to work in a wet environment which can otherwise them ineffective. There also exists a need for systems that allow user to selectively position thermogenerators (hot packs and cold packs) at specific body locations when desired to provide warmth and cool down as desired.

SUMMARY OF THE DISCLOSURE

The present disclosure advantageously fills the aforementioned deficiencies by providing waterproof and breathable thermoregulatory systems.

In one aspect, the present disclosure is directed to a thermoregulation system comprising: a thermoregulation device, the thermoregulation comprising: a receiver and a thermogenerator, the receiver comprising: a first receiver end, a second receiver end, and a receiver channel extending therebetween, wherein the receiver channel is configured to removeably receive the thermogenerator; a fastener configured to selectively close at least one of the first receiver end or the second receiver end; wherein the receiver comprises a waterproof and breathable fabric; and a garment comprising a plurality of panels configured to selectively receive the thermoregulation device.

In one aspect, the present disclosure is directed to a thermoregulation system comprising: a thermoregulation device, the thermoregulation device comprising: a receiver and a thermogenerator, the receiver comprising: a first receiver end, a second receiver end, and a receiver channel extending therebetween, wherein the receiver channel is configured to removeably receive the thermogenerator; a fastener configured to selectively close at least one of the first receiver end or the second receiver end; an outer layer comprising a breathable material; and an inner layer comprising a waterproof material; and a garment comprising a plurality of panels configured to selectively receive the thermoregulation device.

The present disclosure now will be described more fully hereinafter with reference to the accompanying drawings, which are intended to be read in conjunction with both this summary, the detailed description and any preferred and/or particular embodiments specifically discussed or otherwise disclosed. This disclosure may, however, be embodied in many different forms and should not be construed as limited to the embodiments set forth herein; rather, these embodiments are provided by way of illustration only and so that this disclosure will be thorough, complete and will fully convey the full scope of the disclosure to those skilled in the art.

DETAILED DESCRIPTION OF THE DISCLOSURE

In one aspect, the present disclosure is directed to a thermoregulation system comprising: a thermoregulation device, the thermoregulation comprising: a receiver and a thermogenerator, the receiver comprising: a first receiver end, a second receiver end, and a receiver channel extending therebetween, wherein the receiver channel is configured to removeably receive the thermogenerator; a fastener configured to selectively close at least one of the first receiver end or the second receiver end; wherein the receiver comprises a waterproof and breathable fabric; and a garment comprising a plurality of panels configured to selectively receive the thermoregulation device.

In one aspect, the present disclosure is directed to a thermoregulation system comprising: a thermoregulation device, the thermoregulation device comprising: a receiver and a thermogenerator, the receiver comprising: a first receiver end, a second receiver end, and a receiver channel extending therebetween, wherein the receiver channel is configured to removeably receive the thermogenerator; a fastener configured to selectively close at least one of the first receiver end or the second receiver end; an outer layer comprising a breathable material; and an inner layer comprising a waterproof material; and a garment comprising a plurality of panels configured to selectively receive the thermoregulation device.

Figure 1:
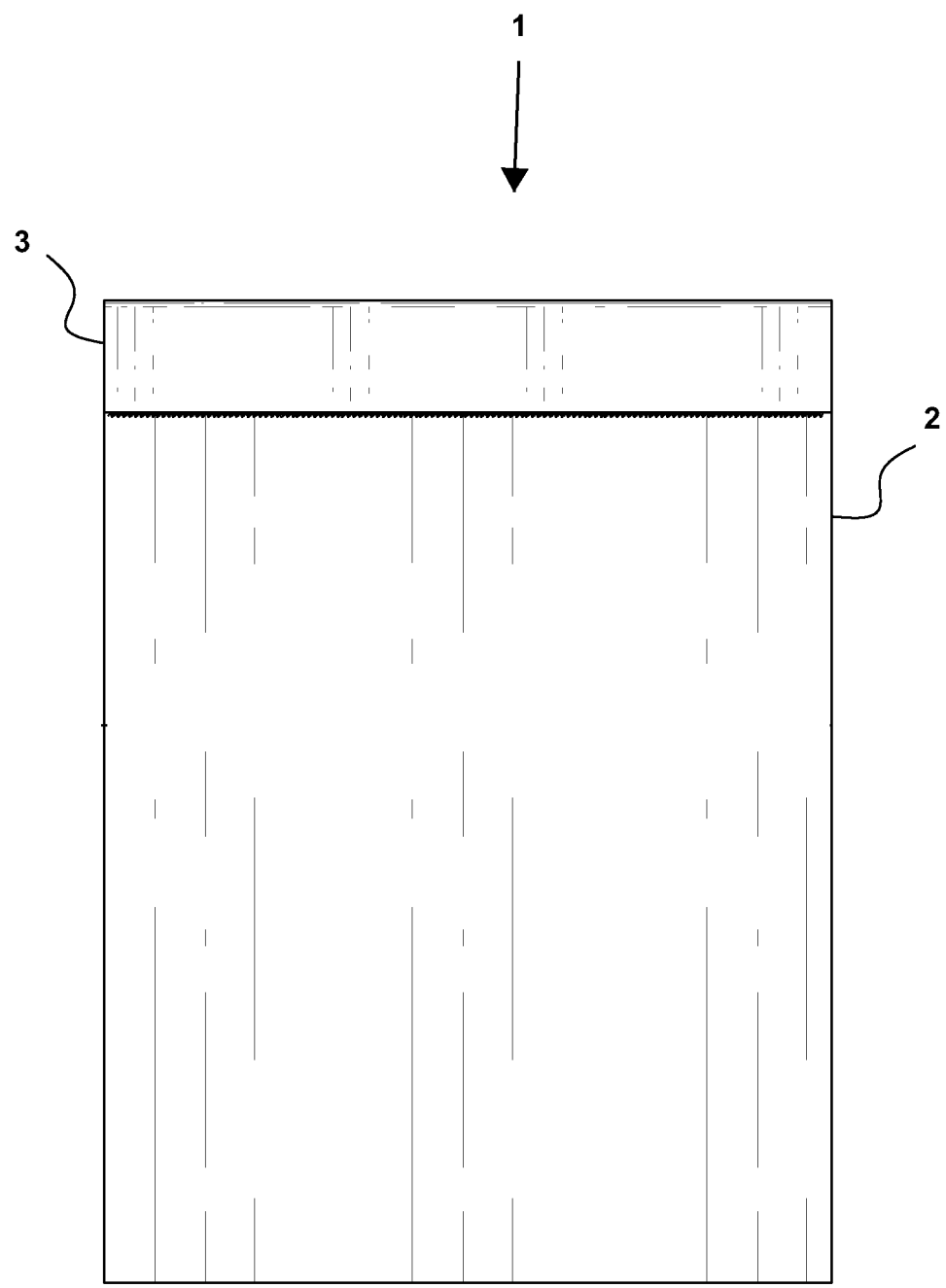
FIG. 1 is a view of the thermoregulation device showing the waterproof and breathable receiver in a closed configuration.
Figure 2:
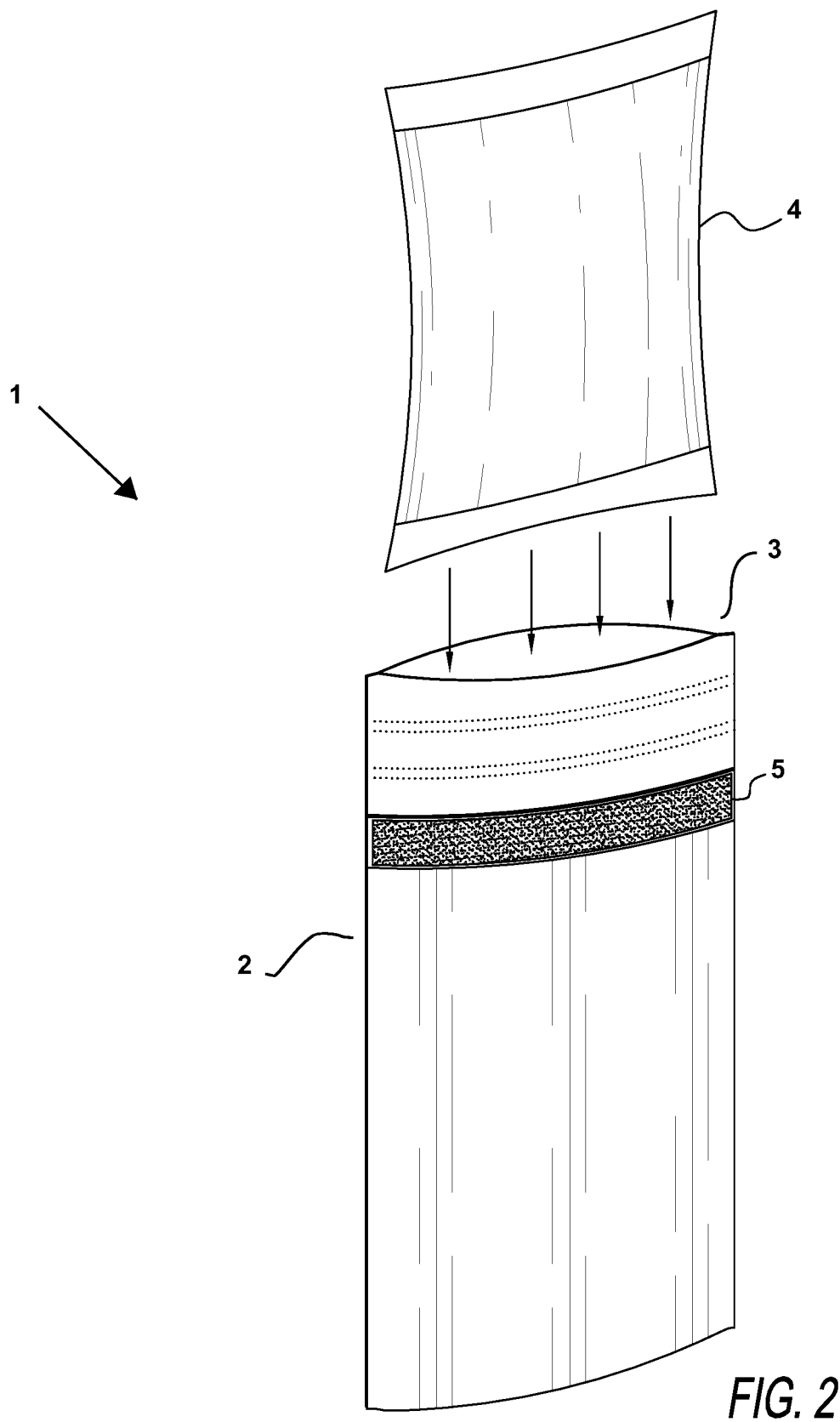
FIG. 2 is a view of the thermoregulation device showing the waterproof and breathable receiver in an open configuration for inserting a thermogenerator.
Figure 3:
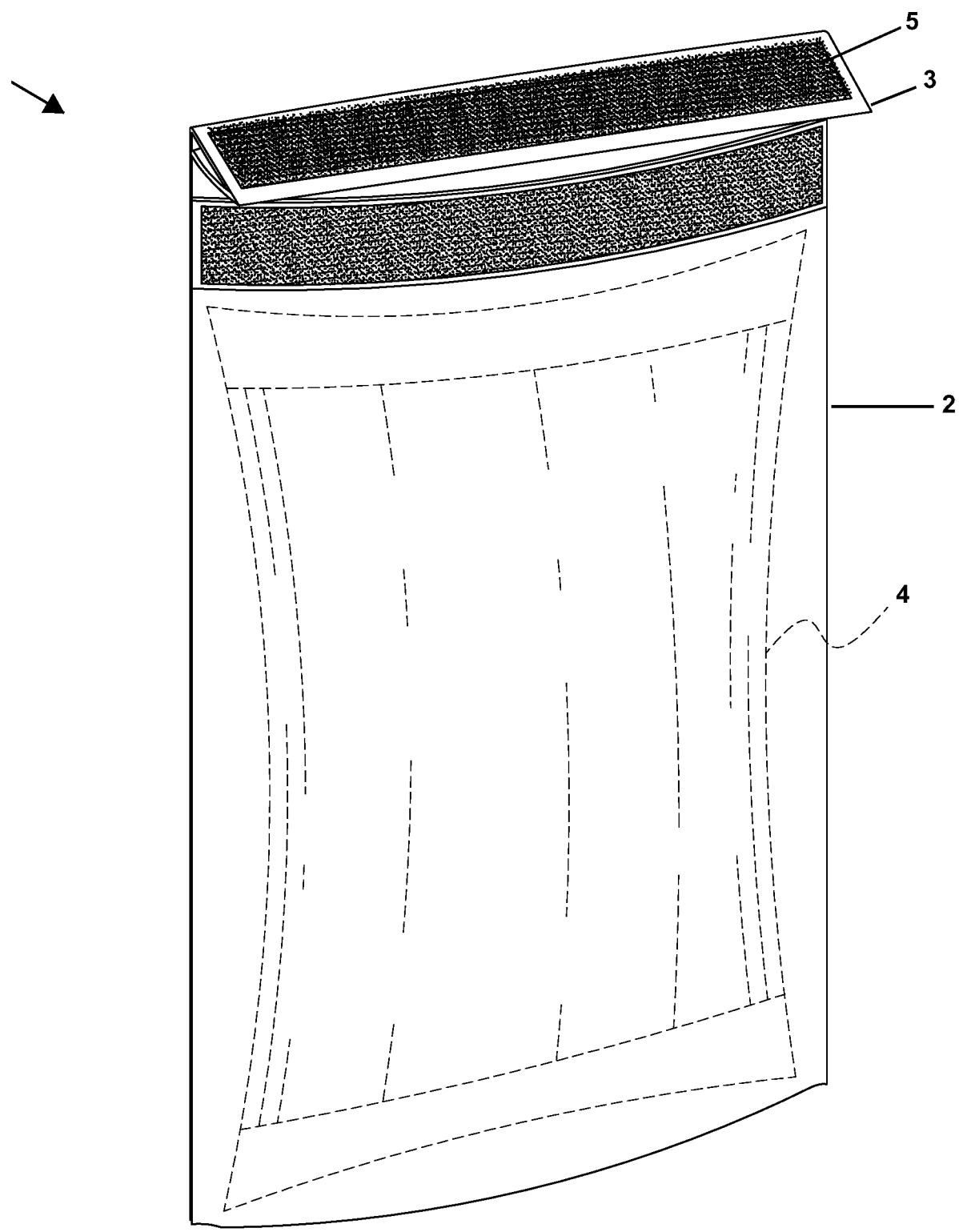
FIG. 3 is a view of the thermoregulation device showing the waterproof and breathable receiver in a partially open configuration illustrating a triple folded embodiment and having a thermogenerator inserted.
Figure 4:
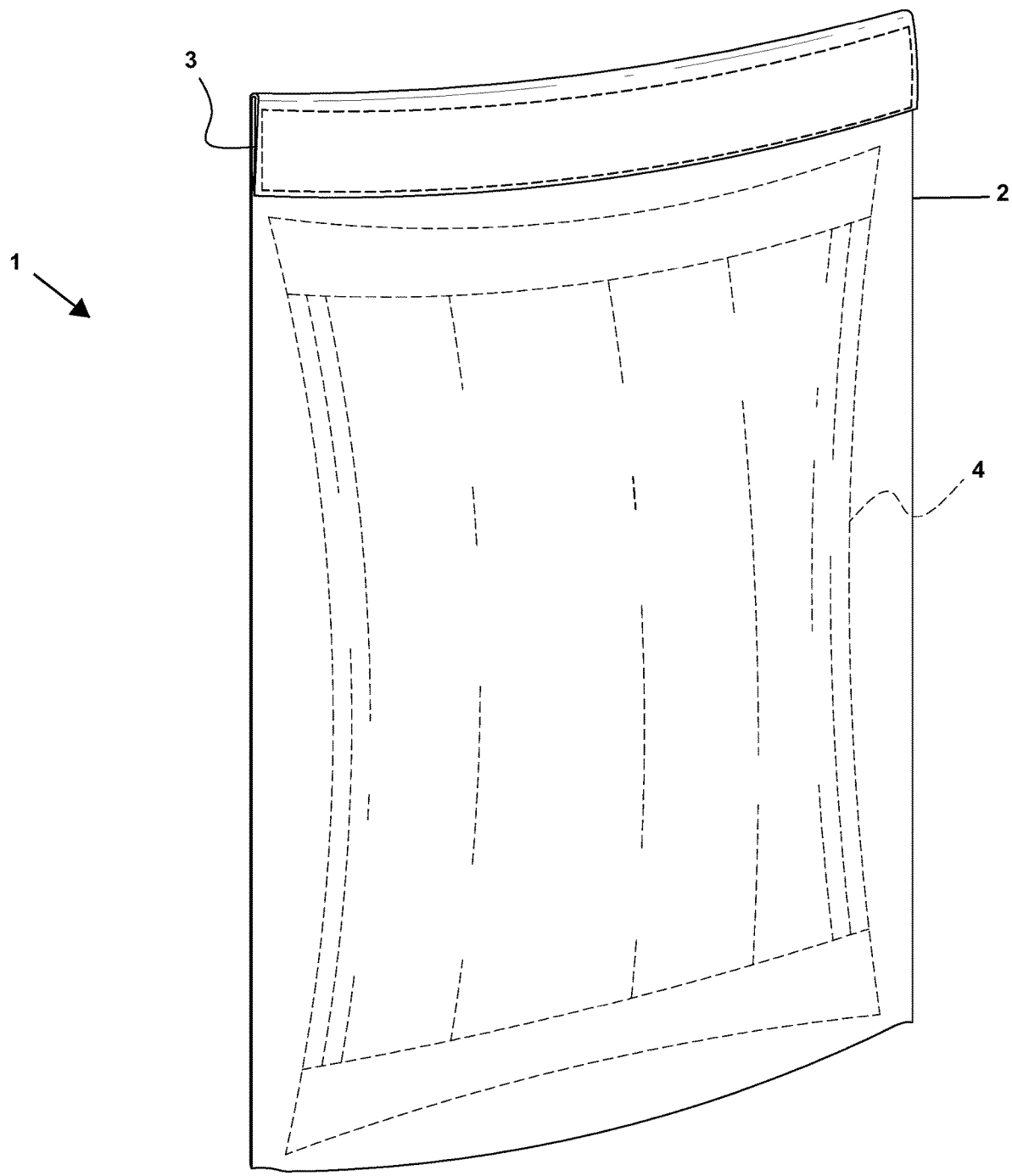
FIG. 4 is a view of the thermoregulation device showing the waterproof and breathable receiver in a closed configuration illustrating a triple folded embodiment and having a thermogenerator inserted.
Figure 5:
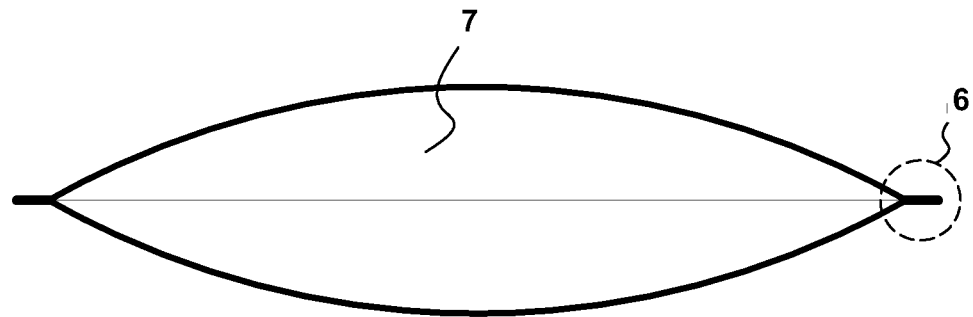
FIG. 5 is a view of the bottom of the thermoregulation device.
Figure 6:
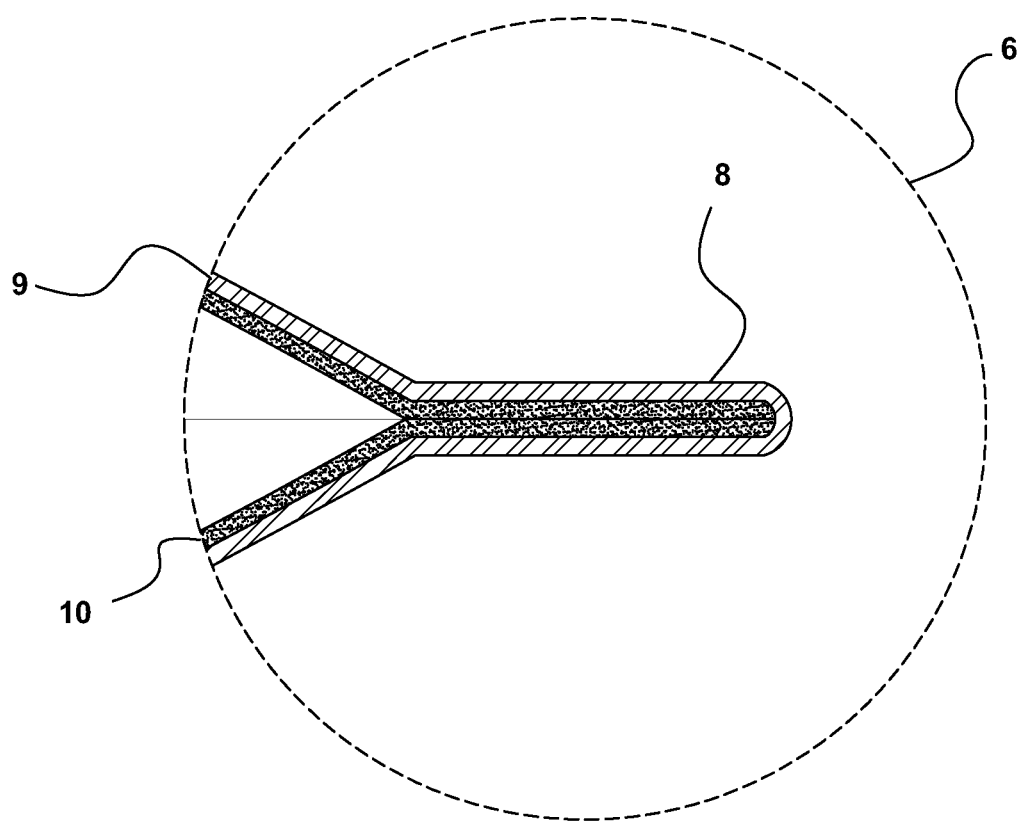
FIG. 6 is an exploded view of the seam portion showing inner layer and outer layer.

FIG. 1 is a front view illustration of the waterproof and breathable thermoregulation device 1 showing the receiver 2 with the first receiver end 3 in a closed configuration. FIG. 2 is an illustration of the waterproof and breathable thermoregulation device 1 showing the receiver 2 with the first receiver end 3 in an open configuration for inserting thermogenerator 4. FIG. 2 shows an illustrative embodiment using a triple-fold hook and loop fastener 5. FIG. 3 is an illustration of the waterproof and breathable thermoregulation device 1 showing the receiver 2 with the first receiver end 3 in a partially closed configuration using a triple-fold hook and loop fastener 5 with thermogenerator 4 within the receiver 2. FIG. 4 is an illustration of the waterproof and breathable thermoregulation device 1 showing the receiver 2 with the first receiver end 3 folded to a closed configuration with thermogenerator 4 within the receiver 2. FIG. 5 is a bottom 7 view of an exemplary thermoregulation device with device edge 6 circled. FIG. 6 is an exploded view of device edge 6 showing overlap 8 of outer layer material 9 and inner layer material 10.

In one embodiment, the thermogenerator comprises a hot pack. As used herein, "hot pack" refers to a sealed pack or container that is filled with chemical reactants for creating an exothermic reaction, as well as those containing liquids and gels that can be warmed up. As known to those skilled in the art, chemical hot packs include magnesium sulfate or calcium chloride. Commercially available air-activated hand warmers contain cellulose, iron, water, activated carbon (evenly distributes heat), vermiculite (water reservoir) and salt (catalyst) and produce heat from the exothermic oxidation of iron when exposed to air. Chemical hot packs are commercially available from a variety of manufacturers such as Bent Grass Concepts, ClickHeat, Dynarex, HEAT WAVE, Hot To Go, and others.

In another embodiment, the thermogenerator comprises a cold pack. As used herein, "cold pack" refers to a sealed pack or container that is filled with chemical reactants for creating an endothermic reaction, as well as those containing liquids and gels that can be cooled. As known to those skilled in the art, chemical cold packs typically use a salt such as ammonium nitrate, ammonium chloride, or urea in one section of the pack and water in another section. Breaking the barrier separating the salt and water allows them to mix, dissolving the salt. As the salt dissolves, it absorbs heat from the air around it, lowering the temperature of the water creating a cooling effect. Suitable cold packs include chemical cold packs, ice packs, and gel packs, as described herein. When used, ice packs can be refrigerated for example in a refrigerator compartment or a freezer compartment to cool or freeze the water component of the ice pack. Similarly, gel packs can be placed in refrigerator compartment or a freezer compartment to cool or freeze the gel component of the gel pack.

As used herein, "waterproof material" refers to a material that resists and/or prevents water penetration therethrough. As used herein "breathable material" refers to a material's ability to allow water vapor to pass through it. Suitable waterproof and breathable materials include coatings or laminations having pores that are so small that liquid water cannot pass through the material, but vapor water molecules are many times smaller than the liquid state and can pass through the material. Fabrics are known to those skilled in the art that can be both waterproof and breathable. In other embodiments, a waterproof and breathable fabric can be made using a layering method in which one layer comprises a waterproof material and a second layer comprises a breathable material. The receiver is made of a material that is waterproof and breathable. Suitable material includes nylon, polyester, elastane, nylon, polyester, elastane, polytetrafluoroethylene material (for example GORE-TEX fabric), and polypropylene filaments blended with elastomeric fibers DuPont COOLMAX®, DuPont LYCRA®, SPANDEX, SYMPATEX and the like. As known to those skilled in the art, materials can be chemically coated to provide waterproofing The fastener is configured to selectively close at least one of the first receiver end or the second receiver end. Any suitable fastener known to those skilled in the art may be used so long as the type of closure used provides protection against water leakage or flow into either receiver end. Particularly suitable fasteners include hook-and-loop, zippers, press and seal (e.g., ZIPLOC®) fasteners, waterproof metal zippers (e.g., YKK® metal zippers), MasterSeal (plastic) zippers. Clamp lock (like used in cell phone waterproof cases. A particularly suitable fastener includes a rubber sealed triple fold hook and loop tape closure. Additionally, at least one receiver end is designed to be folded on itself, such as triple-folded, to provide protection against water leakage or flow into the receiver end. Optionally, fabrics and materials can be lightweight, colorfast, sunfast, abrasion resistant, wind resistant, stain resistant, odor resistant, mold resistant, mildew and microbe resistant, as well as possessing high tensile strength, dye-sublimated, colorable and combinations thereof.

The thermoregulatory device is completely seam locked except for at least one receiver end configured to allow for the thermogenerator to be removably received. The receiver of the thermoregulatory device allows products like personal chemical heaters to continue to breathe while keeping them dry. The waterproof breathable fabric used in conjunction with seams that can be glued, stitched, welded and combinations thereof to ensure they are water-tight as well as the fastener to close an end of the receiver keeps water out of the thermoregulatory device. Desirably, seams are glued.

Figure 7:
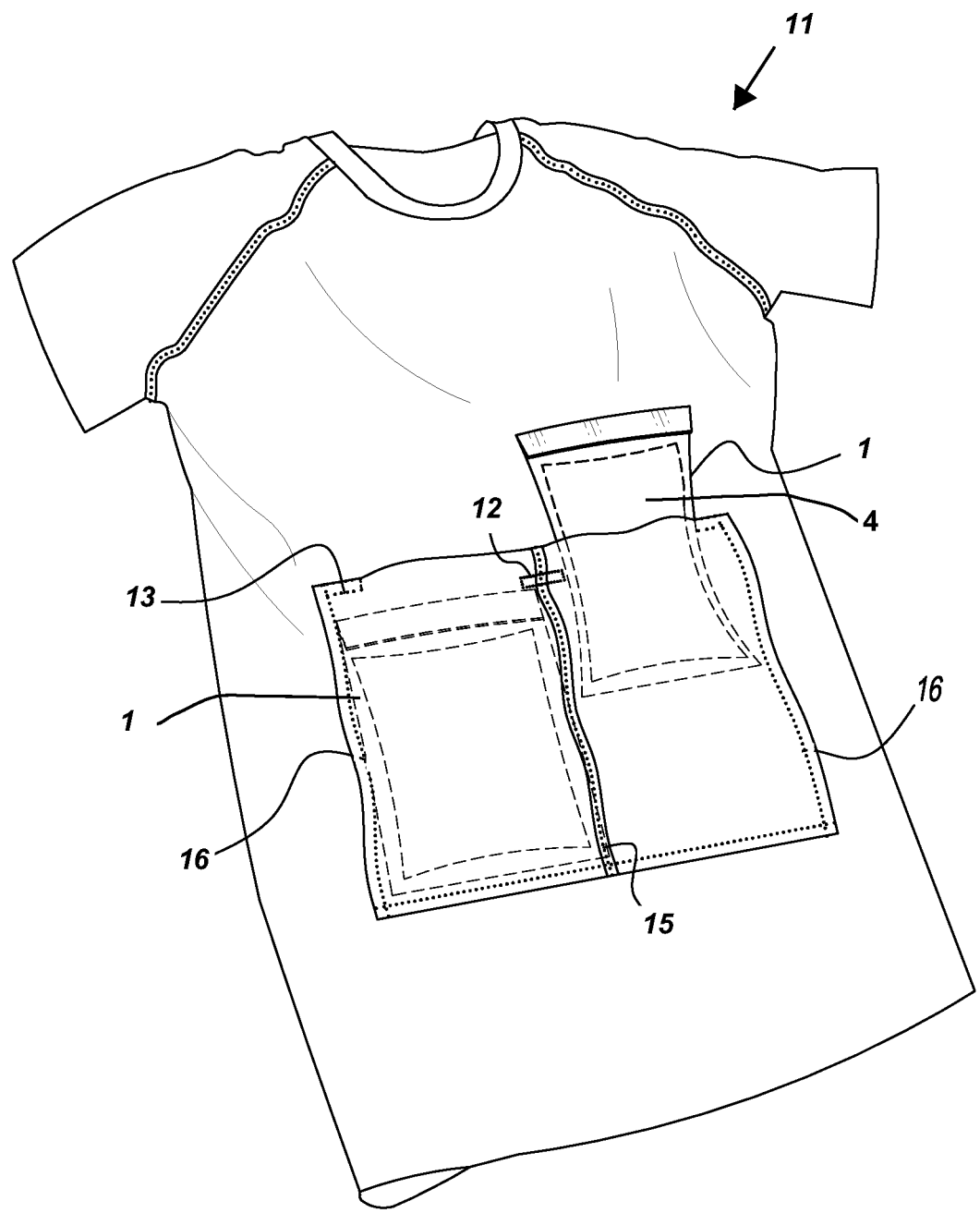
FIG. 7 shows an embodiment of the thermoregulation system having a garment with two front panels with one thermoregulation device fully inserted in one panel and one thermoregulation device partially inserted in one panel.
Figure 8:
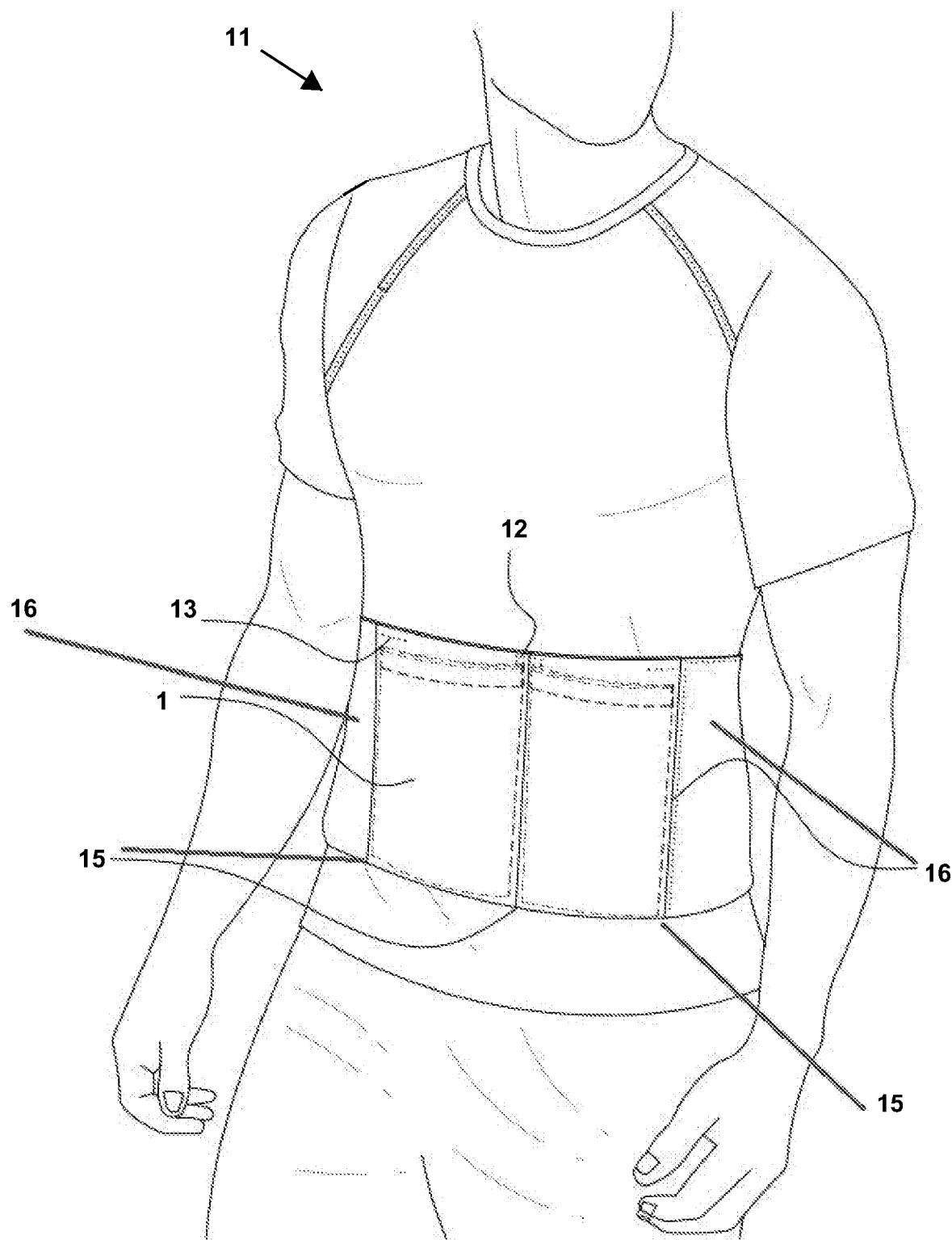
FIG. 8 is a front view showing an embodiment of the thermoregulation system on a user wherein the garment has a plurality of panels. Two front panels contain thermoregulation devices fully inserted the panels and two empty side panels.

Referring to FIG. 7, the thermoregulation device is particularly useful with a garment 11 that includes a plurality of panels 16 configured to removeably receive the thermoregulatory device 1. The panels 16 (as in FIGS. 7 and 8) of the garment 11 are preferably sized for receiving the thermoregulatory device 1 and have an opening for the user to insert the thermoregulatory device. As illustrated in FIGS. 7 and 8, the opening of panel 16 can include a cross-stitch 12 and/or be partially sewn 13 closed so that the user can insert the thermoregulatory device 1 into the panel 16. Cross-stitch 12 and/or sew 13 (FIGS. 7 and 8) further retain thermoregulatory device 1 in panel 16. Partitions 15 can also be sewn into the panels to hold the thermoregulatory device in place. The use of removable thermoregulatory devices 1 provides the additional benefit of being able to use the garments on a day-today basis by transferring the thermoregulatory devices to another garment while one is being washed or laundered. Thermoregulatory device 1 having a thermogenerator 4 is completely contained within panel 16 and held in place by cross-stitch 12, sew 13 and partition 15. FIG. 8 illustrates an exemplary embodiment of a garment on a user having two panels 16 containing thermoregulatory devices 1, which are held in place by cross-stitch 12, sew 13 and partition 15.

Figure 9:
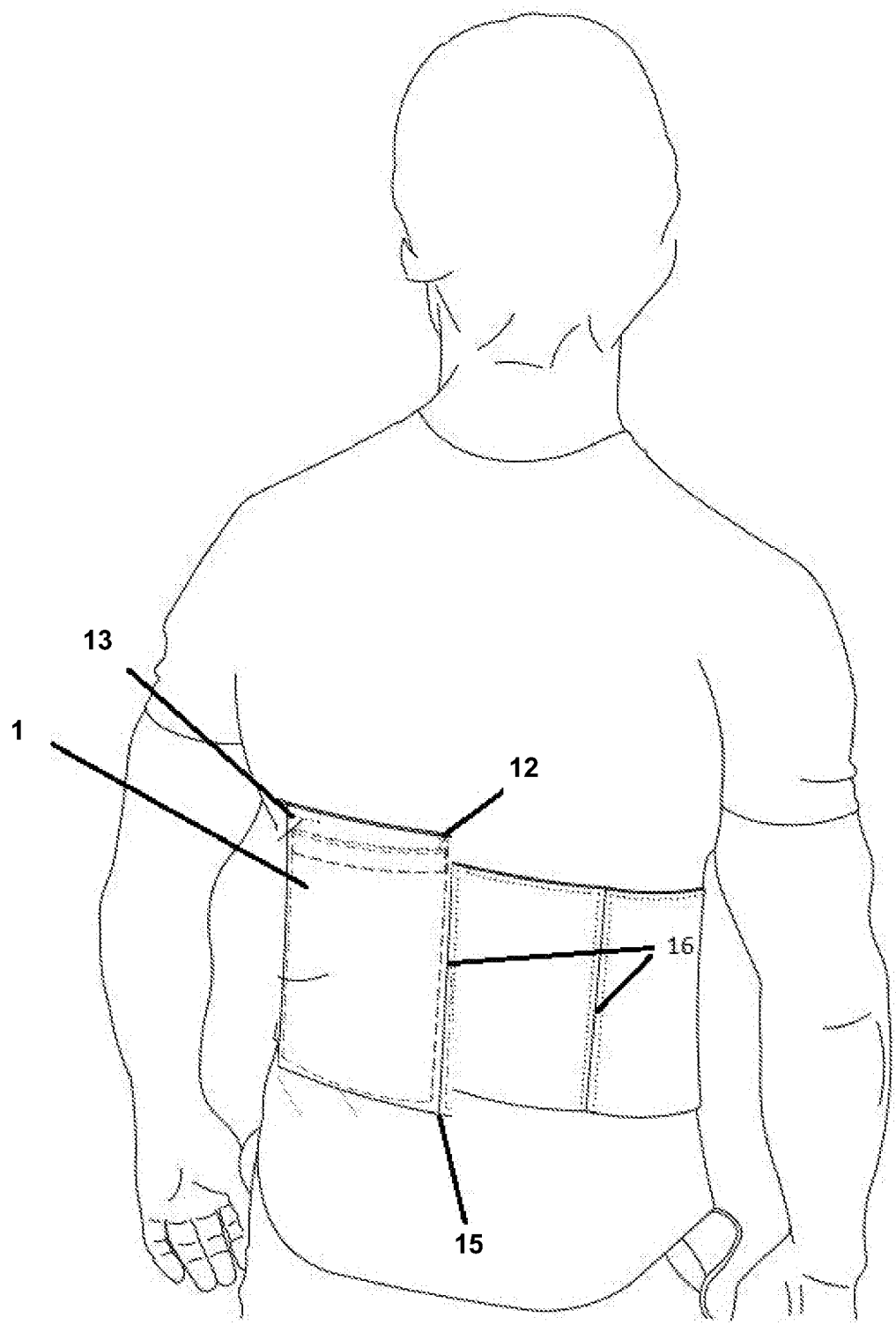
FIG. 9 is a back view showing an embodiment of the thermoregulation system on a user wherein the garment has a plurality of panels. One panel contains a thermoregulation device fully inserted the panel and two panels are empty.

Garments have a plurality of panels. In particular, garments can have one, two, three, four, five or more panels. Exemplary embodiments illustrated in FIGS. 7 and 8 illustrate garment 11 having two panels 16. As illustrated in FIGS. 8 and 9, panels 16 are desirably located on the garment such that thermoregulatory device is positioned at the abdominal region and lower back region of the user. Panels can be located on the front, sides, and back of the garment. Panels can be joined to the garment using methods known to those skilled in the art, such as using sewing techniques, gluing techniques, welding techniques, and combinations thereof.

Suitable garments include shirts and vests. The garments can be made of different types of fabrics. Particularly suitable garments are those that will hold the thermoregulation device close to the body and made of a material that dries quickly so that the heat transfers to the user's body (where warming the user is desired) or from the user's body (where cooling the user is desired) more effectively. Stretchable fabrics and materials are suitable. Compression-type garments are particularly suitable.

Compression garments can be made from elastic fabrics, inelastic fabrics and combinations thereof, and apply a more or less uniform compressive force to the underlying tissue. The compressive garments also hold the thermoregulatory devices closer to the user's body to more effectively transfer heat to the user's body (where warming the user is desired) or from the user's body (where cooling the user is desired).

The thermoregulatory devices can be included in many different types of design applications and have a few different optional features added to them.

The thermoregulation systems of the present disclosure are particularly advantageous to help a user maintain body temperature even while going in and out of water, which can inactivate chemical reactants for generating heat. Among other things, the thermoregulation systems will continue to function even when the user is consistently active and unable to actually hold the warmers and is in and out of water that does not suffer from any of the problems or deficiencies associated with prior solutions. Anyone who is constantly in and out of the water and exposed to cold water and/or air can benefit from the use of the thermoregulation systems of the present disclosure. Exposure to a combination of water and cold greatly increases the risks of hypothermia. As such, individuals such as water sport athletes (surfers, paddle boarders, wave runner riders, fishermen, obstacle, and adventure racers) and those in the military, such as Navy Seals, can benefit from this product.

In use, the thermoregulation systems allow a user to selectively position the thermoregulation device in any of the panels of the garment as desired. For example, when the user desires warmth, thermoregulation devices can be selectively positioned in front panels of the garment. Positioning thermoregulation devices in front panels of the garment provide warmth generated by the thermogenerators, as well as block wind from the abdomen. Should the user become too warm, she or he can selectively position thermoregulation devices in side panels of the garment by removing the thermoregulation devices from the front panels and transferring them to the side panels. The user can position the thermoregulation devices as desired, thus achieving thermoregulation.

While the present disclosure has been described above in terms of specific embodiments, it is to be understood that the disclosure is not limited to these disclosed embodiments. Many modifications and other embodiments of the disclosure will come to mind of those skilled in the art to which this disclosure pertains, and which are intended to be and are covered by both this disclosure and the appended claims. It is indeed intended that the scope of the disclosure should be determined by proper interpretation and construction of the appended claims and their legal equivalents, as understood by those of skill in the art relying upon the disclosure in this specification and the attached drawings.

What is claimed is:

1. A thermoregulation system comprising:
   a thermoregulation device, the thermoregulation device comprising: a receiver and a thermogenerator,
      the receiver comprising:
         a first receiver end, a second receiver end, and a receiver channel extending therebetween, wherein the receiver channel is configured to removably receive the thermogenerator;
         a triple fold hook-and-loop fastener configured to selectively close at least one of the first receiver end or the second receiver end;
         wherein the receiver comprises an outer layer comprising a nylon that is chemically coated to provide waterproofing while still maintaining breathability; and an inner layer comprising a material having pores that are so small that liquid water cannot pass through the material, but vapor water molecules can pass through the material and being selected from the group consisting of polytetrafluoroethylene, polyether-ester block copolymer and combinations thereof, wherein the inner layer is encapsulated within the outer layer;

the thermoregulation device is seam locked with a seam that extends around the receiver with an exception that at least one of the first receiver end and the second receiver end is not seam locked, the seam being watertight; and a garment comprising a plurality of panels configured to selectively receive the thermoregulation device.

2. The thermoregulation system of claim 1, wherein the thermogenerator comprises a hot pack.

3. The thermoregulation system of claim 2, wherein the hot pack comprises one of a chemical hot pack and a gel pack.

4. The thermoregulation system of claim 1, wherein the thermogenerator comprises a cold pack.

5. The thermoregulation system of claim 4, wherein the cold pack comprises one of a chemical cold pack, an ice pack, and a gel pack.

6. The thermoregulation system of claim 1, wherein the plurality of panels comprise a stretchable material.

7. The thermoregulation system of claim 1, wherein the garment comprises a compression material.

8. The thermoregulation system of claim 1, wherein the garment comprises a stretchable material.

9. The thermoregulation system of claim 1, wherein the receiver is configured such to provide thermoregulation over a period of time and after submersion in water.

10. The thermoregulation system of claim 1, wherein the plurality of panels are configured to disrupt airflow thereby selectively aiding in the retention of heat from a user's body.

11. A thermoregulation system comprising:
a thermoregulation device, the thermoregulation device comprising: a receiver and a thermogenerator, the receiver comprising:
a first receiver end, a second receiver end, and a receiver channel extending therebetween, wherein the receiver channel is configured to removably receive the thermogenerator;
a fastener configured to selectively close at least one of the first receiver end or the second receiver end;
an outer layer comprising a material selected from the group consisting of nylon, polyester, polypropylene filaments blended with elastomeric fibers and combinations thereof; and
an inner layer comprising a material having pores that are so small that liquid water cannot pass through the material, but vapor water molecules can pass through the material and being selected from the group consisting of polytetrafluoroethylene, polyether-ester block copolymer and combinations thereof, wherein the inner layer is encapsulated within the outer layer;

the thermoregulation device is seam locked with a seam that extends around the receiver with an exception that at least one of the first receiver end and the second receiver end is not seam locked, the seam being watertight; and a garment comprising a plurality of panels configured to selectively receive the thermoregulation device.

12. The thermoregulation system of claim 11, wherein the thermogenerator comprises a hot pack.

13. The thermoregulation system of claim 11, wherein the thermogenerator comprises a cold pack.

14. The thermoregulation system of claim 11, wherein the garment is chosen from a shirt and a vest.

15. The thermoregulation system of claim 11, wherein the garment comprises compression material.

16. The thermoregulation system of claim 11, wherein the garment comprises a stretchable material.

17. The thermoregulation system of claim 11, wherein the plurality of panels comprise a stretchable material.

18. The thermoregulation system of claim 11, wherein the fastener is a triple fold hook-and-loop fastener.

* * * * *